(12) United States Patent
Trobat et al.

(10) Patent No.: US 9,945,832 B2
(45) Date of Patent: Apr. 17, 2018

(54) APPARATUS AND METHOD TO DETERMINE GROUND PROPERTIES BY TRACTION ANCHORS AND SENSORS

(71) Applicants: Damian Bover Trobat, Colonia de San Jordi (ES); Volker Nannen, Norden (DE); Georgina Ramirez Camps, Barcelona (ES)

(72) Inventors: Damian Bover Trobat, Colonia de San Jordi (ES); Volker Nannen, Norden (DE); Georgina Ramirez Camps, Barcelona (ES)

( * ) Notice: Subject to any disclaimer, the term of this patent is extended or adjusted under 35 U.S.C. 154(b) by 415 days.

(21) Appl. No.: 14/635,693

(22) Filed: Mar. 2, 2015

(65) Prior Publication Data

US 2015/0247835 A1 Sep. 3, 2015

(30) Foreign Application Priority Data

Mar. 3, 2014 (ES) .................................. 201430286

(51) Int. Cl.
*G01N 33/24* (2006.01)

(52) U.S. Cl.
CPC ....... *G01N 33/24* (2013.01); *G01N 2033/245* (2013.01)

(58) Field of Classification Search
CPC .................... G01N 33/24; G01N 2033/245
See application file for complete search history.

(56) References Cited

U.S. PATENT DOCUMENTS

2006/0107772 A1* 5/2006 Shinn, II ............... G01N 33/24
73/864.43

* cited by examiner

*Primary Examiner* — Kyoung Lee
(74) *Attorney, Agent, or Firm* — Notaro, Michalos & Zaccaria P.C.

(57) ABSTRACT

A system and apparatus for determining soil properties and managing the ground can include a platform equipped with traction anchors, wherein at least one anchor is configured to provide a point of traction on the ground and to pull the platform. The system also includes one or more sensors positioned and configured to detect ground properties near the anchor, and a computer subsystem configured to receive and process data on ground properties measured by the sensor, to process this information, and capable of transmitting information about the ground soil to a remote receiver.

19 Claims, 5 Drawing Sheets

APPARATUS AND METHOD TO DETERMINE GROUND PROPERTIES BY TRACTION ANCHORS AND SENSORS

RELATED APPLICATIONS

Priority is claimed to Spain Patent Application No. P201430286, filed on Mar. 3, 2014, which is fully incorporated by reference.

FIELD AND BACKGROUND OF THE INVENTION

The present invention relates to a system that is configured to measure ground and soil properties through sensors which are located in the vicinity of traction anchors, where these anchors periodically make a firm and static contact with the ground to generate traction for a platform, a ground engaging tool, or a load to be pulled. The sensor data is processed by a computing system and either offered to the user, or used to manage the ground in an semi-autonomous or autonomous manner. The invention is applicable to work that relates to the ground, such as agriculture and forestry, civil engineering, mining, clearing space of obstacles, and geotechnical studies.

The measurement and control of ground properties are extremely important to the management of crop, water and soil. For example, ground properties affect:

The production of biomass, in particular the root growth of crops, the spread of pathogens, the availability of water and nutrients, and crop yield.
Infiltration and storage of water, the filtering and leaching of nutrient, pesticides, and harmful substances.
Stability and erodibility of soils.
Production, storage and release of gases like $CO_2$ that affect the climate.
Storage and protection of flora and fauna.
Trafficability for vehicles.
Drawbar strength, energy consumption, and lateral deviation of ground engaging implements like tillage implements.
Suitability of ground for construction.
Value for mining of minerals and fuels.
Conservation of fossils and archaeological artifacts.
The motion in the ground of dangerous objects like buried explosive mines.

The combination of specific ground properties affects, in general, the health status and the quality of soil, and the ability of soil to function as a living ecosystem, to enable civil engineering projects, and to positively influence the climate and the quality of groundwater.

Ground properties referred to by the present invention comprise, preferably but not limited to other properties: slope, the type of material that covers a soil surface, temperature, moisture content, water storage capacity, infiltration rate, texture, structure, cementation, porosity, size of the hard lumps, clay content, type and amount of organic matter, depth and distribution of roots, the presence, state and activity of earthworms, nematodes, ants, termites and other animals, the presence, state and activity of microorganisms, bacteria, fungi and weeds, the content, state and availability of nitrate, phosphate, potassium, iron, boron and other macro and micronutrients, aluminum, lead and other toxins, other minerals, the amount and composition of atmospheric air and other gases, alkalinity, salinity, pH, electrical conductivity, the dielectric permittivity, soil strength, stone content, the dry bulk density, the depth of the topsoil, the vadose zone, the water table, and the presence of distinct horizons or layers that, for example, facilitate or hinder the movement of water and minerals and growth of roots.

Knowledge of ground properties is also useful for the following activities:

Decide the time, location, type and depth of operations such as tillage, planting, irrigation, fertilization or pesticide application, and to select the appropriate tillage tools, such as moldboads, cultivators, discs, chisels, cylinders, harrows, or subsoilers.
Predict soil degradations like erosion, compaction, and contamination, and take measure to prevent them.
Nivellation and terassing.
Find, study, and preserve archaeological sites.
Deciding the location and depth of drainage pipes and other pipes and electric cables, fiberoptic cables and other cable that are laid on the ground or buried in the ground, for example, to allow optimal drainage, to protect them from harm or to minimize environmental interference.
Dig trenches, and stabilize and maintain banks of bodies of water.
Locate valuable minerals.
Find a suitable way for navigation and transport, and avoid or engage obstacles such as rocks or mines.
Manage ecological, geological and climatic systems: depending on ground properties, it can be determined whether certain types of land management will be advantageous or have drawbacks. Land management that leads to carbon sequestration, for example, may be advantageous since it mitigates global warming. Meanwhile, land management which leaches pesticides may be inadvisable, because it contaminates groundwater.
Achieve persistent autonomy for autonomous devices, since the degree of autonomy of an autonomous device depends on the knowledge that is available on the state of its environment. Trafficability for example depends on the firmness of the soil.
Decide on the depth of soil to be removed, how to contain and neutralize contaminants and how to assess the risk of leaching.

Some ground properties such as clay content tend to be stable over many years and do not need to be measured frequently. Other properties, such as soil water content can change significantly from day to day and frequent measurements may be of economic advantage, for example to control irrigation. Some ground properties like clay content can change dramatically within a meter's distance and call for high resolution measurements, while other properties like pH are stable over dozens of meter and call for measurements of lower resolution.

Measuring ground properties requires time and resources. Measurements such as soil temperature at depth are best taken in-situ and require penetration of the ground by a probe. Some ground sensors must have a good physical contact with the ground and have a non-zero response time. For example, it takes about 10 seconds to obtain a useful reading of an ion selective electrode.

Ground properties are often measured with hand held tools or with a dedicated vehicle that stops regularly in the field to penetrate and probe the ground. Non-stationary work like tillage, earth moving, or transport of cut trees is normally done with diesel tractors, because of their efficiency and robustness. It is impractical to measure ground properties with sensors that need to be stationary during such non-stationary work, since to halt and accelerate a diesel tractor carries a significant cost in time and energy consumption. When stopped, a diesel tractor that plows or drags a load performs no useful work.

During normal operations of a non-stationary tractor all parts of the tractor system move over or through the ground at a relatively high speed, so that it is technically challenging to establish permanent ground contact for any length of time. The company Veris Technologies in the United States is a leader in soil sensing technology and perhaps the only provider of on-the-go chemical soil analysis. One product offered by this company measures chemical soil properties such as pH by extracting soil samples from a moving vehicle, and the samples are analyzed on the vehicle. There is no solution that chemically analyzes a sample of soil in-situ while the vehicle moves and tills the soil or pulls a load.

Variable depth plowing promises to save substantial amounts of energy by plowing only to the depth that is really needed. It depends on the ability to measure soil strenght at different depths. Soil strength can be measured during plowing operations by combining a measurement of speed over the ground with the reading of dynamometers that are connected to the drawbar. But this method does not allow identification of soil strength at different depths. Another method to measure soil strength is to use pressure sensors in the tillage tool itself. However, this greatly complicates the design of the tillage tool, which is generally subject to heavy wear, and can interfere with the tillage operation.

The present invention aims to solve the above technical problems, which characterize the devices and methods that form the state of the art.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

SUMMARY OF THE INVENTION

An object of the present invention is a system that allows to overcome the problems of the state of the art described above, by a system (for example a platform, a plow, a blade, or a skidder) which is moved by a traction mechanism, wherein the force of said traction is generated by anchors or crampons which periodically establish a firm grip on the soil or ground and which remain static while another part of the system moves forward. The general characteristics of a traction mechanism for anchors are described, for example, in United States patent application 20130112441. In the case of the means of traction of the present invention, and in difference to other known traction systems by anchors, the anchors are preferably equipped with a plurality of sensors of ground properties, and while the anchors cling to the ground to provide the necessary support or foothold to generate traction, the sensors remain long enough in sufficient proximity to a portion of the ground, such that the properties of this portion of the ground can be measured, like for example electrical conductivity or pH value. When the anchors penetrate the ground, the sensors can also penetrate the ground with the anchor and measure the ground properties at depth, as well as the penetration resistance of the ground at different depths from the force needed to drive an anchor into the ground.

More preferably, the invention relates to a system according to the independent claim or any of the dependent claims included in the present patent application, which describe the main novel features that characterize the invention.

DESCRIPTION OF THE PREFERRED EMBODIMENTS

Figure 1:
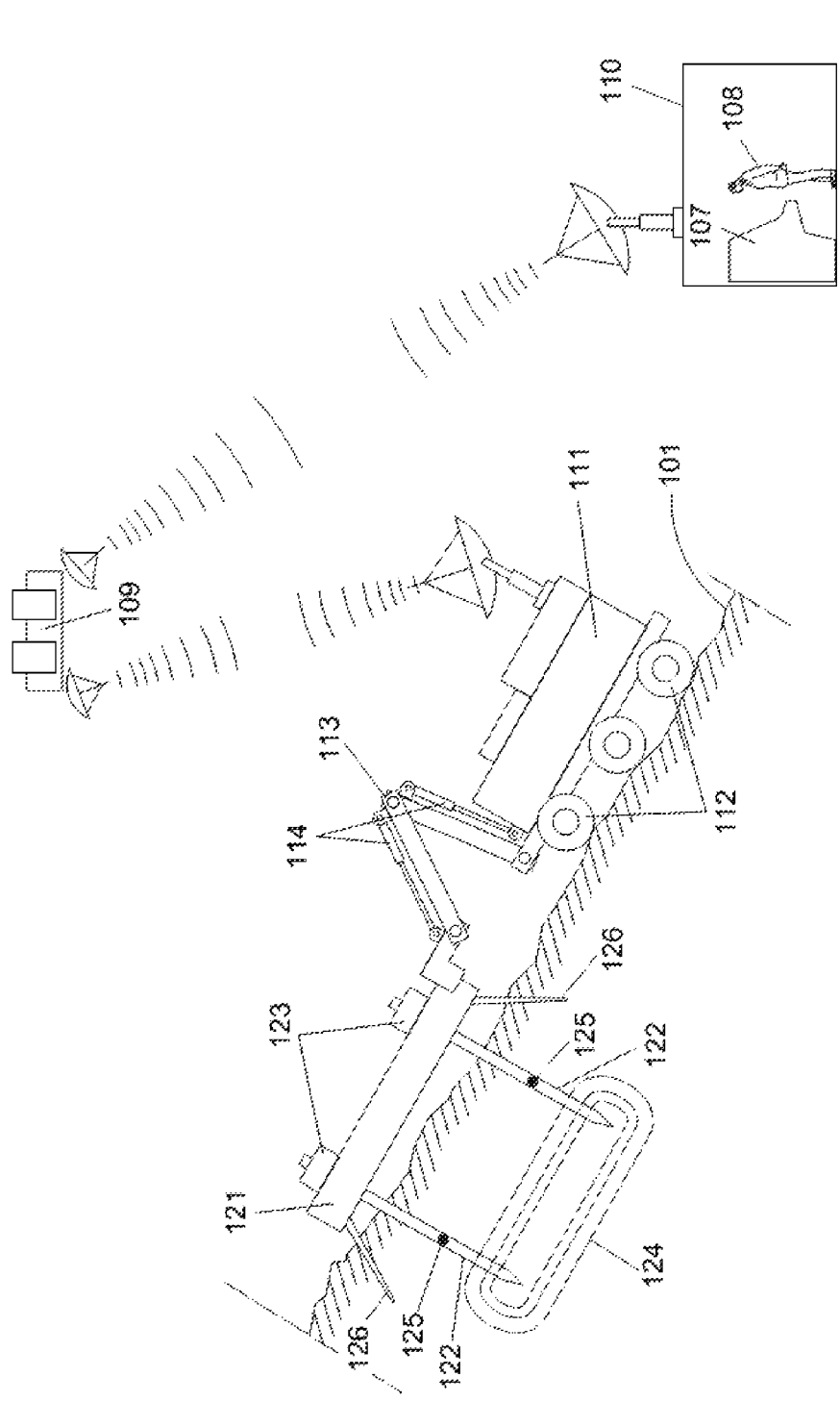
FIG. 1 shows an exploration platform in difficult terrain, wherein said platform is supported by wheels, according to a preferred embodiment of the system described by the present invention.

The object of this invention is a system composed of a platform that combines measurement of ground properties with anchors that provide at least some of the traction to pull the platform, a ground engaging implement, or a load.

The moving platform can roll, slide, or otherwise move over or through the ground. The load being pulled can be a vehicle or for example a cut tree.

The ground engaging implement can be, for example, a tillage implement or a tool to place a pipe, neutralize a mine, a blade for clearing, leveling, or terracing soil, or a tool to dig trenches or shape embankments.

The ground can be, for example, sand, farmland, rock, ice, snow, mineral deposit, seabed, terasses, banks of trenches and other bodies of water, of or a mound of forage, minerals or municipal waste.

We pass now to describe the main elements of the Invention:

The Traction Anchor

A traction anchor, which can also be called a crampon, or simply anchor, provides traction to pull or push a platform, or a ground engaging implement, or a load, while it is static for a non-zero period of time and while it is in firm contact with the ground, possibly penetrating the ground, such that the total amount of rearward motion resistance that the anchor experiences is greater than the forward motion resistance of what is pulled or pushed.

The anchor is connected to the platform, ground engaging implement, or a load by an extension shaft, an articulate arm with joints, a telescopic system, a rope, or by other means. When power is applied to extend or contract this connection while the anchor has a firm grip on the ground, the platform, ground engaging implement, or load is moved in the desired direction.

A traction anchor has a number of advantages over wheels or belts: On soft ground, a tire loses up to 45% of energy due to slippage, motion resistance, and tire flexing. Traction by anchor can save this energy. Anchors can also increase the overall stability of a system, preventing it from tipping over or sliding down a slope, such that it allows operation on steep inclinations, on soft surfaces, and with uneven distributed loads under conditions that are unsuitable for wheeled vehicles. An anchor also provides the necessary operating conditions for ground sensors that have a non-zero response time, require firm contact with the ground, or need to penetrate the ground to a certain depth.

An anchor can achieve motion resistance by penetrating the ground, in which case the resistance depends, among other factors, on the depth in the ground, the strength of the penetrated ground, the angle in the ground, the surface, and the geometry of the penetrating anchor. As a rule, a deeper penetration, a more vertical angle in the ground, a rough surface, and a bluff, non-streamlined geometry of the penetrating body of the anchor all increase motion resistance. An anchor can also achieve motion resistance by clamping to a static object such as a tree or a rock. It can clamp with hooks, flukes, teeth, grapples, screws, magnets, van der Waals force, suction, and by other means.

A system can use one or more actuators to drive an anchor into the ground, and pull it out of the ground. The anchor may enter or leave the ground with pressure, rotation, vibration, or other actions. The force for driving the anchor into or out of the ground can be electrical, hydraulic, pneumatic, suction, or other. The type and amount of force required per unit of depth to move the anchors in or out of the ground can be measured as a parameter of the ground.

An anchor can also penetrate the ground as a result of being pushed or pulled. In that case, when a horizontal force is applied to the anchor, for example from a load to be pulled as in FIG. 2, initially this force pulls the anchor towards the load. By applying a second downward force to the anchor, for example from its own weight, the combined forces can push the anchor diagonally into the ground. As the anchor enters deeper into the ground, motion resistance increases, until the anchor has more motion resistance than the load, and the load is being pulled. As the anchor enters deeper into the ground, it can also right itself by pivoting about a joint, as described in FIG. 2, further increasing motion resistance.

It is fundamental to the principle of traction by anchor that the part of the system which provides traction has a motion sequence that is different from the part of the system which is pulled. The anchor periodically moves faster than other parts of the system, is placed in position, and is then kept static, while the anchor pulls forward other parts of the system, a ground engaging implement, or a load.

When the anchor does not pull, what is being pulled can be stationary because of its own motion resistance, or move forward by itself with less force, or move backward, losing some of the progress made with the anchor.

The anchor may be part of the steering mechanism of the system. If the anchor is placed in the intended direction, it will pull the system in that direction. The system can also be steered by some other means, either while not anchored, for example by support wheels or tracks, or while anchored. Steering may also be applied while the anchor pulls, for example by directed wheels, by a rudder, or by controlling the lateral difference in motion resistance of what is pulled. If the system is steered while the anchor pulls, it helps if the connection between the anchor and the rest of the system has one or more vertical joints, to reduce torque on the anchor.

More than one anchor may be used. The anchors can be operated together or independently. For example, one anchor may provide traction while another anchor is being pulled forward and being anchored, and vice versa. In this case there is less interuption of the motion of the platform, a ground engaging implement, or a load.

The anchor may have a special surface to control friction and wear. The anchor may have a tip of a special material and geometry to help in the measurement of the penetration resistance. The anchor needs to be made of a material that is strong enough to withstand the different forces acting on the anchor, including pressure, shear force, and torque.

The anchors can be structurally combined with a ground engaging implement or with a load. For example, an implement can be shaped such that the motion resistance at the front is low and at the back is high, such that when pulled forward, it will plow through the ground, acting as a tillage tool, but when pulled backward, it will remain static and act as an anchor. Or, by changing the inclination of an implement or load, or by vibrating it, the motion resistance of an implement or load can be changed such that in one configuration it has a high motion resistance and acts as an anchor, and in another configuration it has a low motion resistance, and can be pulled through or over the ground.

The stability of anchors can extend the range of ground measurements to difficult terrain. For example, in soft soil or on steep slopes, such as banks of trenches and other bodies of water, agricultural terasses, steep forest lands, volcanoes or meteorite craters, the traction of wheels or tracks may not provide enough traction, and the platform may become stuck, tip over, or fall. Wheels and tracks also provide insufficient stability for excavators and cranes, which are dangerous to operate when clearing banks of bodies of water, and in forestry. In wet climate the traction of ballasted tires causes compaction damage to agricultural crops. Anchors can overcome such difficulties, allowing work on steep slopes and very wet environments.

The energy efficiency of anchors can extend the range of ground measurements to areas where energy consumption is a limiting factor. It can, for example, help to explore deserts or other areas remote from supplies, and it can help in extra-planetary exploration. While the system can be powered with conventional combustion engines, the energy efficiency of the traction system also encourages battery or solar panel operation.

The Sensors

Fixation of an anchor provides a ground sensor with operational stability. The sensor may be integrated in the actuator of the anchor, the anchor itself, or be adjacent to it. It may operate in physical separation from the anchor, but still benefit from the stability provided by the anchor to measure ground properties. The sensor can be configured to measure the ground properties at the surface and/or at depth while the anchor is not inserted into the ground and/or at depth as the anchor is inserted into the ground.

The sensor may enter and leave the ground together with the anchor or independently. When integrated in the anchor, the part that makes contact with the ground can be a part of the surface of the anchor, protrude from it, or be in a cavity. It can be left unprotected or protected when not in operation. The forces inherent to the operation of the anchor can be used to establish the necessary contact with the ground or the sensor can be provided with its own actuator to establish that contact. The sensor can be cleaned by friction with the ground, by water, by vibration, or by other cleaning mechanisms. The sample of ground that is close to the sensor can be prepared prior to measurement for example by vibrating the anchor. This is particularly effective if the sensor is located in a cavity.

Some sensors or parts of sensors need no physical contact with the ground, but can be operated from a distance, such as radar, or from the interior of the anchor, such as induction coils.

Sensors that measure ground properties include, among others, thermometers, pressure sensors, accelerometers, penetrometers, inclinometers, vibration sensors, capacitive sensors, electrodes, ion selective electrodes, induction coils, neutron moisture gauges, tensiometers, spectrometers, optical sensors, acoustic sensors, and radar. Other sensors from those known in the art may equally be used within the scope of the present invention, such as sensors of ground properties that are mechanical, electromagnetic, chemical, optical, acoustic and/or radioactive.

Sensors can be passive or active. The sensors may have various parts that interact with the signals. Interactions include emitting a signal, filter, delay, reflect, transform or transduce or measure a signal. For example, a portion of a sensor may emit white light and another part measures the color of reflection. Or one part induces a primary current and another part measures a secondary current. These different parts of the sensor can be associated with different anchors. For example, the induction and the measurement of electrical currents in the ground can be distributed across several anchors. A portion of the sensor may be external to the anchor or platform, while another part is near the anchor.

An anchor might not hold firm after all, but might move slightly while measurements are taken. For example, in wet soil, the entire area around the anchor can move, and when holding onto a rock, the rock may move. This movement of the anchor can be measured or inferred from other data and can be used to correct or to discard the data measured at the anchor, or to treat it probabilistically. This movement can be treated as a parameter of the ground.

The Computer Subsystem

A computer subsystem collects and stores (e.g., in electronic, magnetic, or optical memory) data from the sensors and can tag it with time and location data. The time and location data can be absolute. They may also be relative to some other measurement or event in the current sequence of operations, or relative to some local landmark of unknown global position. Location data can be obtained from an inertial measurement unit, compass, radar, sonar, camera images, fixed beacons, signals from satellite (GPS) or unmanned aerial vehicles, altimeters, and other methods on the platform or outside of it.

The various location data and the various data from ground sensors can be processed to improve, for example, transport, storage, continuity, precision, reliability, robustness and accessibility of data. Data processing includes compression, normalization, interpolation, combination, fusion, and filtration. Data processing may process data collected at the anchor as possibly influenced by motion of the anchor.

Pedotransfer functions can be used to estimate ground properties that are relatively difficult to measure from the ground properties that are relatively easy to measure. For example, clay content can be estimated from electrical conductivity.

Localized data can be organized into a map, and can be combined with data and maps that are external to the current collection of ground data, like data on the work to be performed, the presence of obstacles, previous ground measurements, crop yield maps, satellite imagery, vegetation cover, or tractor tram lines. This forms a geographic information system (GIS), and its data can be combined with data from other GISs, or feed data to other GISs.

Location sensors, the computer subsystem that collects and stores data and the processing unit which processes the data, and the computer subsystem that combines data into maps and combines different maps may be located on the platform, or may be in a different location and communicate with the platform, for example through a wireless network or via a cable bus, continuously or at intervals.

Autonomy

The system can be operated by a human being, or operate in semi-autonomous or fully autonomous mode.

A computer subsystem can decide and control the path to be followed, the measurements to be taken, the work to be done, and other actions, based on a work plan provided by the user, data collected currently or previously, external data, and operational preferences and heuristics. The computer subsystem can evaluate the actions after execution.

A computer subsystem can use the raw or processed data to make decisions about the operation of the system. For example, the soil strength at different depths can be used to decide the depth of tillage. Or, to decide whether the ground is too soft to be traveled, and should thus be avoided.

The computer subsystem can detect a number of inconsistencies in a number of portions of the ground and control the reduction of the inconsistencies. For example, the system can detect a portion of the ground that is too acidic and apply lime, or it can detect a portion of the ground which is too wet, and put drainpipes.

The computer subsystem can use the sensor data to control the rate of variable crop inputs in an agricultural application, including tillage depth, seed density, the amount of irrigation, and the application of fertilizers, weed control, and insect control. It can also make decisions on optimal seed variety, tillage tools, and other discrete factors.

An information system may present the data raw or processed to the user. The information system can also present and propose different possible actions to the user in a comprehensible manner, and the user can choose one of the presented options, or define a new action.

According to the embodiments shown in FIGS. 1-5, which accompany the present document, FIG. 1 shows a semi-autonomous exploration platform (111) in rough terrain (101) that is soft and steep. The platform is supported by wheels (112) which are equipped with brakes (not shown). An articulated arm (113) with piston actuators (114) extends forward with an anchor frame (121). The anchor frame has two anchors (122), which penetrate the ground and can pull the vehicle through difficult portions of the terrain. The anchors have actuators (123) that vibrate the anchors while they are inserted into the ground. The force to insert the anchors into the ground and extract them from the ground is supplied by electrical motors (not shown). Integrated into the anchors are electrical coils and contacts (not shown) that create an electrical field (124) and measure electromagnetic properties. Other sensors on the anchor surface (125), and close to them (126) measure chemical properties such as pH. All measured values are sent to a satellite (109), which also localizes the platform and tags the data with coordinates. The data is then sent to a control station (110), where a computer subsystem (107) stores, processes, and displays the data to a scientist (108). The scientist uses the processed data to plan the next step of exploration.

Figure 2:
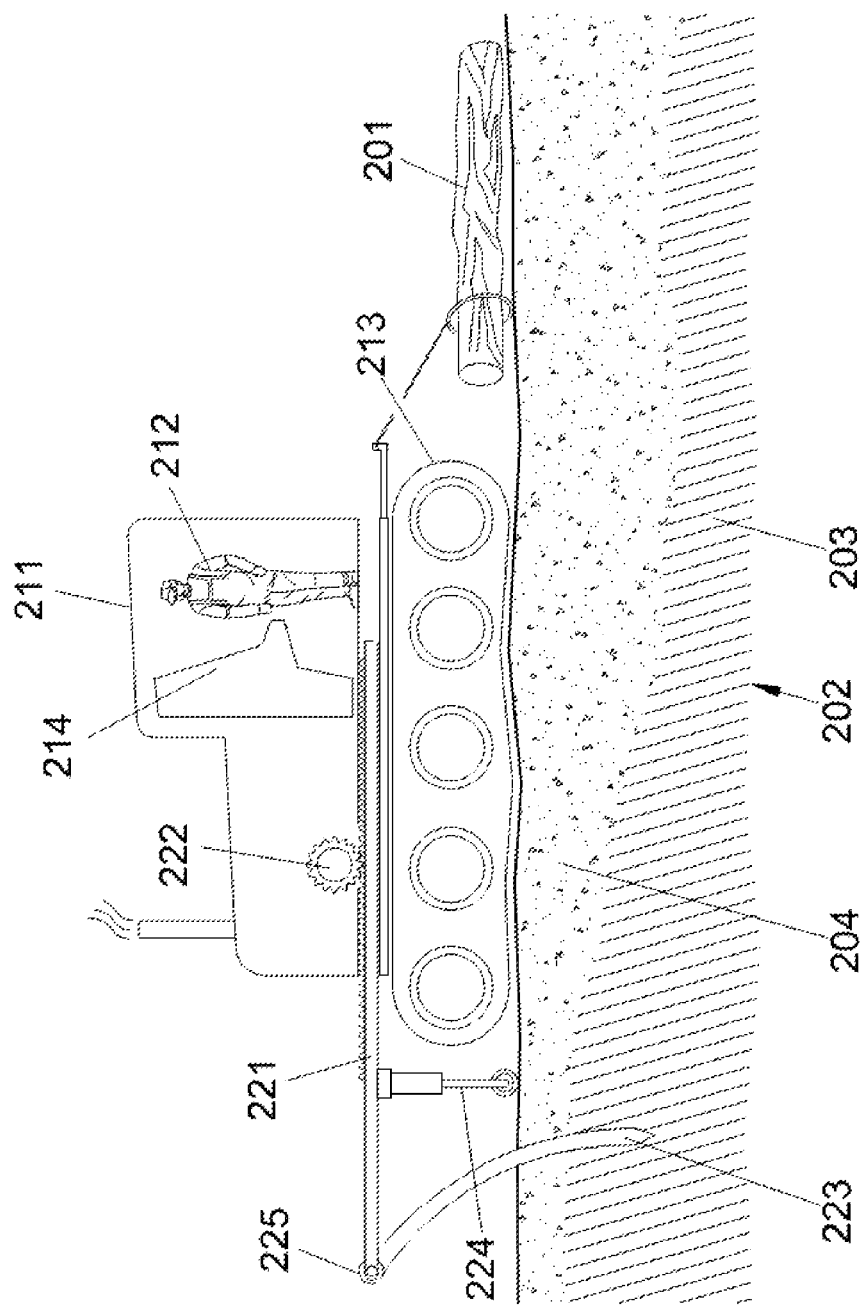
FIG. 2 shows a platform for pulling a cut tree, according to a preferred embodiment of the system described by the present invention.

FIG. 2 shows a platform (211), also called a skidder, which pulls a cut tree (201) over ground (202) consisting of soft mud (203) covered with a frozen layer (204) of ice and mud. The thickness of the frozen layer is not uniform. The platform is operated by a human (212). The platform is supported by tracks (213). A telescopic arm (221) driven with a toothed wheel (222) extends forward with claw-shaped anchors (223). The anchor is attached to the arm by a hinge (225) that allows the anchor to be rotated into the ground when it is pulled back, and can rotate out off the ground when pushed forward. When it is pulled back, it first penetrates the ground and with increasing depth in the ground pulls the platform and the load. A system of sensors (224) at the end of the arm consists of a suspension system that measures the height, and a wheel that measures motion.

A sensor (not shown) in the hinge (225) measures the angle. The combination of these sensors measures the depth of penetration of the anchor, and if the anchor remains fixed in the ground. An information system with graphical display (214) shows the measurements to the human operator. If the anchor is not stable, the frozen layer is not thick enough, and the human operator will use the tracks to reorient the vehicle and try a different path.

Figure 3:
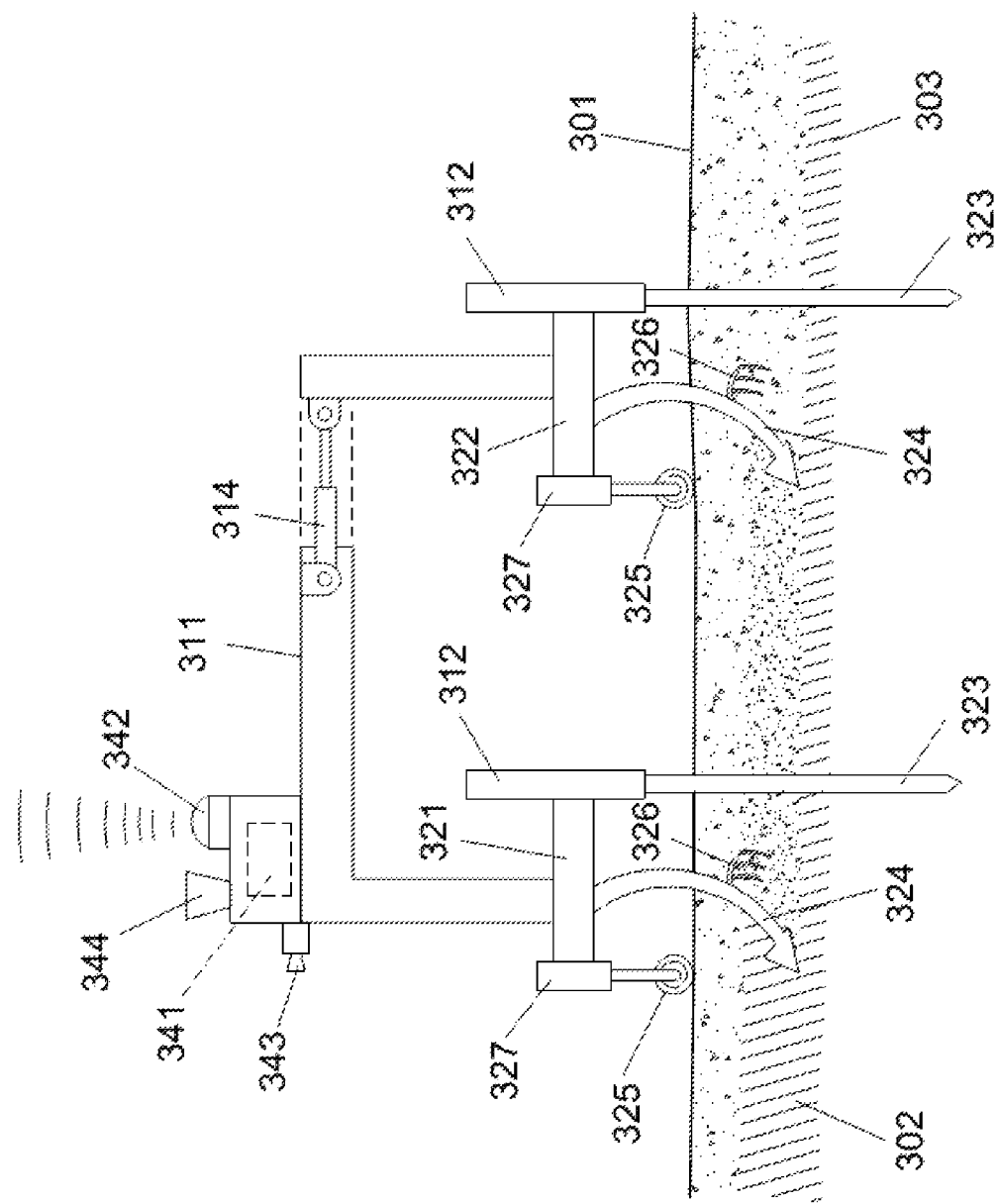
FIG. 3 shows a platform which tills the soil, according to a preferred embodiment of the system described by the present invention.

FIG. 3 shows an autonomous platform (311) which plows the soil (301). The soil has a hard layer (302) which can impede the growth of crop roots. The platform has a frame (321) in front with anchors (323), plows (324) and wheels for depth control (325), and a similar frame (322) in the rear with anchors, plows and wheels for depth control. The plows have support anchors (326) in the rear to increase rearward motion resistance. When pulled forwards, these support anchors are in the shadow of the plows and do not have motion resistance. When pulled backwards, they stick into the ground and increase backward motion resistance of the plows. The wheels for depth control have hydraulic actuators (327) that control the depth of the plows. The two frames are connected by a telescopic arm with a hydraulic actuator (314). In an alternating motion pattern one frame places the anchors and pulls or pushes the other frame, which plows the soil. The anchors are placed in the ground by hydraulic actuators (312). Sensors (not shown) on the plows measure electrical conductivity at different depths. Sensors integrated into the hydraulic system (not shown) detect the hydraulic pressure per unit depth of the anchors. The front anchors are aligned with the rear plows and vice versa (not shown). For this reason the front anchors measure soil strength before the work of the rear plows and the rear anchors measure soil strength after the work of the front plows. A computer subsystem with an autonomous planner (341) collects data and detects a hard layer (302) and whether some of this layer (303) remains after plowing. The computer subsystem sets the actuators of the depth control wheels so that the plows destroy the hard layer, but do not go deeper into the soil.

When it rains, a rain gauge (344) on top of the vehicle measures the amount of rainfall. The computer subsystem combines this information with measurements on the change in the electrical conductivity at different depths, allowing it to map the water permeability in the ground.

The computer subsystem also utilizes soil parameters, GPS (342) and a camera (343) to localize itself in the field, in order to decide on a work plan that includes a path for plowing, and in order to follow this path.

In FIG. 3 the telescopic arm (not drawn to scale) has extended to the maximum, and the front anchor has just penetrated the ground, while the rear anchor is still penetrating the ground. The rear anchor will now be extracted from the ground, and the telescopic arm will contract to pull the rearward plow forward through the soil.

Figure 4:
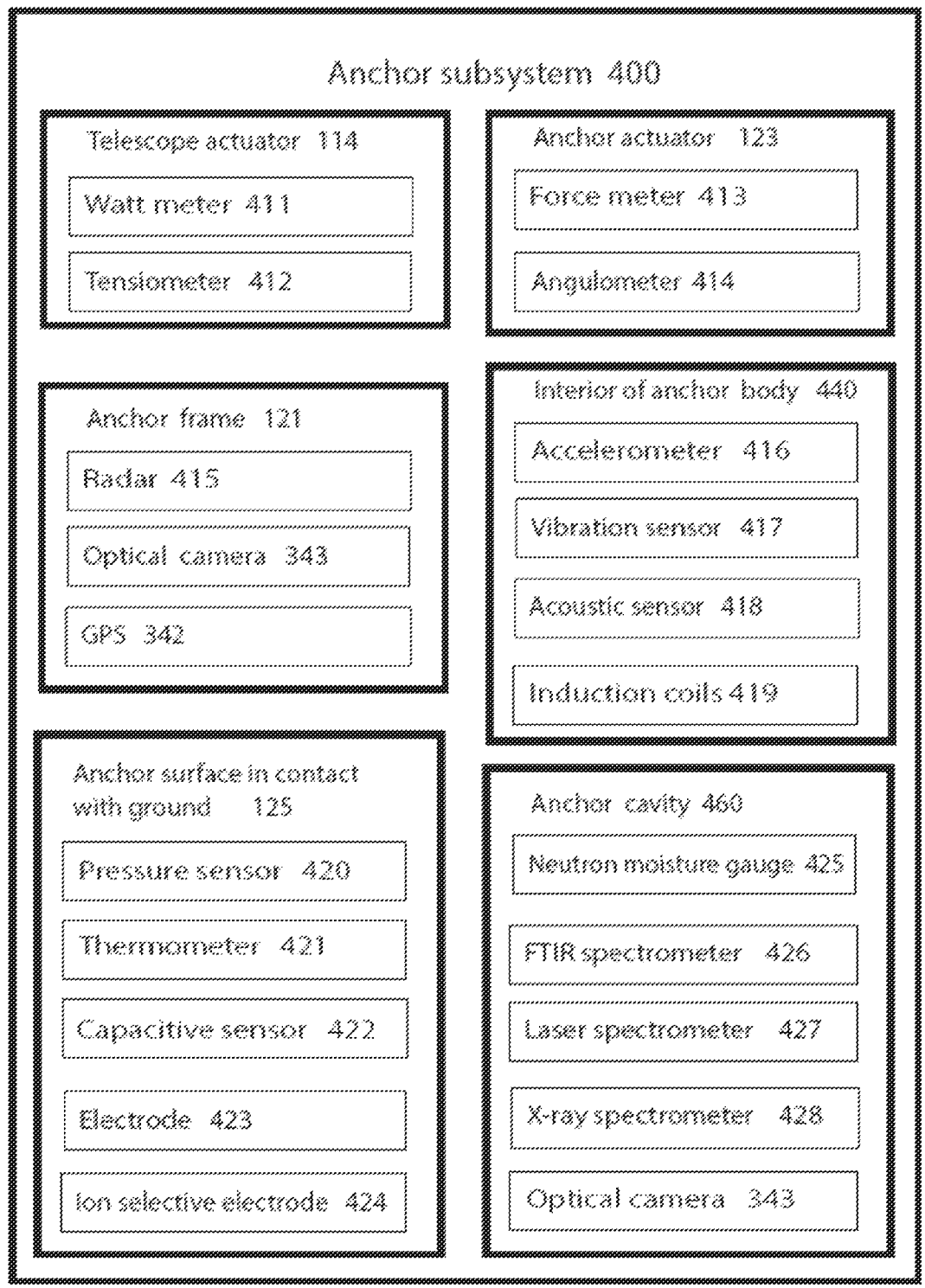
FIG. 4 illustrates a possible configuration of sensors around different parts of the anchor subsystem.

FIG. 4 illustrates by way of a diagram how the different sensors can be distributed over the different parts of the anchor traction subsystem. Other distributions are also possible. Actual sensors will be selected according to the application, and whether a sensor is placed for example on the anchor surface or in a cavity will depend on factors like abrasiveness and stickiness of the ground. The connectors, the wiring, its shielding, the design of the electronic bus and interfaces are not shown, but should take into account the abrasive nature of ground contact and the strong possibility of signal interference. These subjects are covered by relevant industry standards such as SAE J1614 and ISO 11783.

On the telescopic subsystem (114), a Watt meter (411) measures power consumption of an electrically driven actuator, and a tensiometer (412) measures the force when pulling a load from the anchor. A force meter or penetrometer (413), an inclinometer (not shown) and an angulometer (414) are integrated into the anchor actuator (123) and measure the penetration resistance and inclination of the anchor when penetrating the ground.

On the anchor frame (121) an optical camera (343) analyzes the type of ground cover, and a ground penetrating radar (415) can detect for example buried obstacles. A global positioning system (GPS) (342) on the frame helps to accurately localize all measurements taken at the anchor.

Within the body of the anchor that penetrates the ground (440) an accelerometer (416), a vibration sensor (417), and an acoustic sensor measure the stability of the anchor and a possible displacement while pulling. An emitting induction coil (419) in one anchor, and a receiving coplanar induction coil (419) in a second anchor measure electrical conductivity to estimate soil water content, clay content, and organic matter content.

On the surface of the anchor (125) and in direct contact with the ground are a pressure sensor (420), and a thermometer (421). A capacitive sensor (422), and an electrode, together with a second electrode on a second anchor, also measure electric conductivity to estimate soil water content, clay content, and organic matter content. An ion selective electrode (424) measures specific chemical soil properties, like for example potassium concentration.

In a cavity (460) in the anchor body, in close proximity to the soil and at some depth, but without being subject to the friction and wear of the anchor surface, a neutron moisture gauge (425), paired with a neutron emitting source in a second anchor, measures soil water content. A Fourier Transform Infrared (FTIR) (426) spectrometer analyses soil organic matter quality. A laser spectrometer (427) detects microbial gases. An X-ray spectrometer (428) detects the presence of heavy toxic metals like lead. An optical camera, together with proper image analysis algorithms, detects macro-fauna like earthworms and larger roots. By using a fiber optic cable, the main parts of the camera can be placed in the anchor frame and only a scratch resistant and non-adhesive lens needs to be present in the cavity. The anchor can be vibrated in order to move a sample of ground into the cavity.

Figure 5:
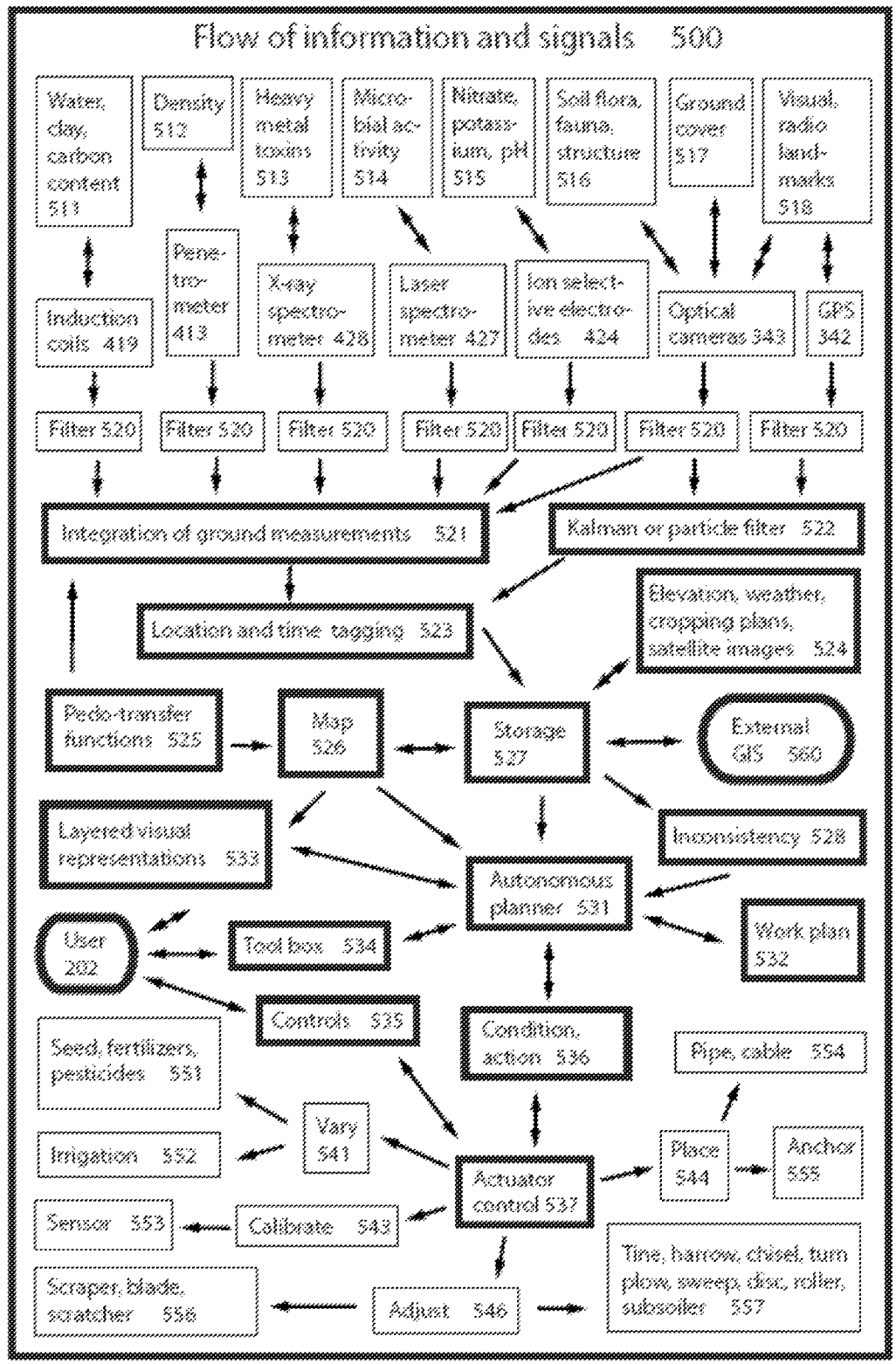
FIG. 5 illustrates a possible flow of information from ground properties to the user and then to the actions that manage or engage the ground.

FIG. 5 illustrates by way of a diagram the main flow (500) of information and signals in a preferred configuration of the system. This diagram is not complete, as important information flows like for example system diagnosis and power control are not included. Other configurations are also possible.

A number of ground properties, in this case water, clay, and soil organic carbon content (511) are measured by induction coils (419) and other electric sensors like electrodes (not shown). Ground density (512) is measured by the penetrometer (413). Heavy metal toxins (513) are measured by the X-ray spectrometer (428). The gas signature of microbial activity (514) is measured by a laser spectrometer (427). Ion-selective electrodes (424) measure nitrate and potassium concentrations and pH (515). Different optical cameras (343) measure the structure, flora, and fauna of soil (516), as well as the type of ground cover (517). Optical cameras (343) are also used to localize the system with respect to visual landmarks (518), while the GPS system (342) uses electronic signals to localize the system with respect to radio landmarks (518) like antennas of the mobile phone network or satellites.

Signal flow between properties and sensors is usually bi-directional. The camera system may for example emit light in order to detect soil properties. The signal received at each sensor passes through individual analogue (for example polarizers) and digital filters (520) before being sent to the computer subsystem proper. While digital filters can be considered the first part of the computer system, they are often already built into commercial sensor systems. These sensors usually integrate several measurements into one, reduce noise, enhance contrast, and compress the signal.

Filtered signals are transmitted to the computer subsystem proper, which is described in figure elements 521-537. The first processing step is the integration (525) of sensor signals into a complex ground measurement. Pedo-transfer functions (525) help to get a first estimate of clay and water content from the different individual measurements of for example induction coils and electrodes. In parallel, different location measurements are integrated to get a more precise location estimate, for example with the help of Kalman or particle filters (522). The soil measurements are then tagged (523) with location and time data, and put into storage (527).

The storage unit (527) contains a growing database of soil measurements at specific times and locations, and a database with information from other sources, like elevation maps, weather information, cropping plans, and satellite images (524), which the system obtains from the user (202) and from external geographic information systems (GIS) (560). The system can share the collected data with external GISs, acting for example as a local weather station. Interpolation methods like Kriging allow the computer subsystem to make multi-dimensional maps (526) of the work area, again using pedo-transfer functions to infer relevant parameters like nutrient availability from the measured data. These maps are then analyzed for inconsistencies (528). For example, a local deficit of potassium can be detected by comparing the measured potassium concentration with what is desirable according to the cropping plan. Inconsistencies that suggest faulty or badly calibrated sensors and that have not become apparent during the preceding steps can also be detected at this level.

The map and the identified inconsistencies are sent to an autonomous planner (531), which maintains a work plan (532). The work plan contains a set of actions as well as conditions when to apply those actions. For example, it can contain a path to follow on the map, and the conditions that define when to adjust the angle of a scraper. It also contains conditions for emergency stops. The planner will incorporate specific actions into the work plan to address the inconsistencies. For example, the rate of potassium fertilizer can be increased, or seed distribution can be reduced. The inconsistency may also necessitate calibration of a sensor. The planner offers to the user (202) a visual map, organized in different layers (533) for the different types of information, so that the user can easily navigate and digest the information. This information includes the measured ground properties, external GIS information, the inconsistencies, and the work plan. The user interface also includes a tool box (534), which contains a number of predefined actions and conditions (536) so that the use can change the work plan if desired, like for example different possible paths to follow, different tillage tools to use for different ground conditions, or the preferred rate of variable crop inputs. The actions and conditions are then broken down into different actuator signals by actuator controllers (537). An actuator controller sends digital or analogue signals to the actuator in question, until the desired state is achieved, or a fault must be acknowledged. The user also has a programming interface and manual controls (535) to directly control the actuators, side-stepping the autonomous planner.

There are different actuator signals for different actions: for seed, fertilizer, and pesticides (551) and for irrigation (552) the signal is a variation (541) in the application rate. For sensors (553), a possible signal is to calibrate (543). Traction anchors (554) and tools to lay pipes and cables (555) receive a location signal (544) that includes the precise coordinates and depth. Signals to adjust height and angles (546) are sent to scrapers, blades, or scratchers (556) and also to tines, harrows, chisels, sweeps, turn plows, discs, rollers, and subsoilers (557).

While a specific embodiment of the invention has been shown and described in detail to illustrate the application of the principles of the invention, it will be understood that the invention may be embodied otherwise without departing from such principles. All reasonable combination and sub-combination of the elements, apparatus, and methods described herein are contemplated and considered disclosed in all reasonable combination and sub-combinations.

What is claimed is:

1. A system to determine ground properties comprising:
a platform equipped with a means for traction by anchors, wherein said means for traction comprises at least one anchor configured to periodically provide static and firm contact with the ground to pull or push another part of the system,
wherein
the anchor comprises one or more sensors of ground properties; and
the system is equipped with a computer subsystem configured with means for at least one of: recording information regarding ground properties measured by the sensor, processing information regarding ground properties, and transmitting information regarding ground properties to a remote receiving device;
wherein the system further comprises an implement equipped with at least one of a seed distributor, a mineral distributor, a fertilizer distributor, a pesticide distributor, and an apparatus configured to irrigate the ground.

2. A system to determine ground properties according to claim 1, wherein the sensors comprise means to at least one of emit, filter, delay, reflect, transform and measure a signal generated by physico-chemical or biological properties of the ground.

3. A system to determine ground properties according to claim 1, wherein the sensors comprise one or more of the following: thermometers, pressure sensors, accelerometers, vibration sensors, capacitive sensors, electrodes, ion selective electrodes, induction coils, neutron moisture gauges, pressure sensors, spectrometers, optical sensors, acoustic sensors, inclinometers, cameras, sonar, radar, sensors of soil strength at different depths, sensors of anchor motion, sensors to measure penetration depth of the anchor and sensors to measure the position of the anchor into the ground.

4. A system to determine ground properties according to claim 1, wherein the sensors of ground properties are at least one of: integrated into the actuator of the anchor; arranged in a region of the anchor which is not inserted into the ground during traction; arranged in a region of the anchor that is inserted into the ground during traction; and arranged in a region adjacent the anchor.

5. A system to determine ground properties according to claim 1, wherein the computer subsystem is configured with means for guiding and applying the anchor based on the information associated with ground properties measured by the sensors.

6. A system to determine ground properties according to claim 1, wherein the computer subsystem is configured with means for global or local localization of the position of at least one of the anchor and the platform.

7. A system to determine ground properties according to claim 1, further comprising a tillage implement positioned to engage the ground, wherein said implement comprises at least one of a tine, harrow, chisel, sweep, turn plow, disc, roller, subsoiler, scraper and scratcher.

8. A system to determine ground properties according to claim 7, wherein the computer subsystem is configured with means to control the tillage implement, based on the information regarding ground properties measured by the sensors.

9. A system to determine ground properties according to claim 1, wherein the platform is connected to and moves with said implement equipped with at least one of a seed distributor, a mineral distributor, a fertilizer distributor, a pesticide distributor, and an apparatus configured to irrigate the ground.

10. A system to determine ground properties according to claim 1,
wherein the computer subsystem is configured with means to control at least one of the following based on information on ground properties measured by the sensors:
the timing, the position, or the depth in the ground at which to distribute at least one of seeds, minerals, fertilizers and pesticides; and the density of at least one of seeds, minerals, fertilizers and pesticides.

11. A system to determine ground properties according to claim 1,
wherein the computer subsystem is configured to:
generate a representation of the ground over which the platform is moving, based on the information measured by the sensors;
identify a number of inconsistencies in a number of portions of the ground over which the platform moves, based on the representation obtained; and
control the distribution of at least one of seeds, mineral fertilizers, pesticides and irrigation in portions of ground over which the platform moves and where inconsistencies are identified.

12. A system to determine ground properties according to claim 1, wherein the system comprises at least one of:
an anchor frame comprising one or more anchors, and an articulated arm having a plurality of piston actuators, with the articulated arm movably connecting the platform and the anchor frame;
a telescopic arm having at least one claw-shaped anchor thereon, and a toothed wheel positioned for driving the telescopic arm; and
two frames connected by a telescopic arm having a hydraulic actuator, and wherein each of the two frames carries at least one respective anchor.

13. A system to determine ground properties according to claim 1, wherein the computer subsystem is configured with means to control the distribution of at least one of pipe and cable based on the information associated with ground properties measured by the sensors.

14. A system to determine ground properties comprising:
a platform equipped with a means for traction by anchors, wherein said means for traction comprises at least one anchor configured to periodically provide static and firm contact with the ground to pull or push another part of the system,
wherein:
the anchor comprises one or more sensors of ground properties;
the system is equipped with a computer subsystem configured with means for at least one of: recording information regarding ground properties measured by the sensor, processing information regarding ground properties, and transmitting information regarding ground properties to a remote receiving device; and
the system comprises an implement to distribute a pipe or a cable in the ground.

15. A system to determine ground properties comprising:
a platform equipped with a means for traction by anchors, wherein said means for traction comprises at least one anchor configured to periodically provide static and firm contact with the ground to pull or push another part of the system,
wherein
the anchor comprises one or more sensors of ground properties;
the system is equipped with a computer subsystem configured with means for at least one of: recording information regarding ground properties measured by the sensor, processing information regarding ground properties, and transmitting information regarding ground properties to a remote receiving device; and
the system comprises at least one agricultural tillage implement selected from: a plow, a tine, a harrow, a chisel, a sweep, a turn plow, a disc, a subsoiler, a blade, and a scraper.

16. A system to determine ground properties according to claim 15, wherein the system comprises at least one of:
an anchor frame comprising one or more anchors, and an articulated arm having a plurality of piston actuators, with the articulated arm movably connecting the platform and the anchor frame;
a telescopic arm having at least one claw-shaped anchor thereon, and a toothed wheel positioned for driving the telescopic arm; and
two frames connected by a telescopic arm having a hydraulic actuator, and wherein each of the two frames carries at least one respective anchor.

17. A system to determine ground properties according to claim 15, wherein the platform is connected to and moves with said at least one agricultural tillage implement.

18. A system to determine ground properties according to claim 15, wherein the computer subsystem is configured to control said agricultural tillage implement based on ground property information from the sensor.

19. A system to determine ground properties according to claim 15, wherein said agricultural tillage implement is configured to at least one of: dig trenches, shape embankments, remove soil, and terrace soil.

* * * * *